United States Patent [19]

Gordon et al.

[11] Patent Number: 5,336,253

[45] Date of Patent: Aug. 9, 1994

[54] PACING AND CARDIOVERSION LEAD SYSTEMS WITH SHARED LEAD CONDUCTORS

[75] Inventors: Pat L. Gordon, Austin, Tex.; John T. Meador, Fridley, Minn.; John G. Keimel, New Brighton, Minn.; Rahul Mehra, Stillwater, Minn.

[73] Assignee: Medtronic, Inc., Minneapolis, Minn.

[21] Appl. No.: 21,408

[22] Filed: Feb. 23, 1993

[51] Int. Cl.$^5$ ............................................. A61N 1/05
[52] U.S. Cl. ..................................... 607/122; 607/128
[58] Field of Search ................ 607/122, 123, 125–131, 607/4

[56] References Cited

U.S. PATENT DOCUMENTS

| | | |
|---|---|---|
| 4,440,172 | 4/1984 | Langer . |
| 4,499,907 | 2/1985 | Kallok et al. ........................ 607/122 |
| 4,595,009 | 6/1986 | Leinders . |
| 4,614,192 | 9/1986 | Imran . |
| 4,726,383 | 2/1988 | Cook . |
| 5,014,696 | 5/1991 | Mehra . |
| 5,044,375 | 9/1991 | Bach . |
| 5,222,506 | 6/1993 | Patrick et al. ........................ 607/122 |

*Primary Examiner*—Lee S. Cohen
*Attorney, Agent, or Firm*—Reed A. Duthler; Harold R. Patton

[57] ABSTRACT

A combined pacing and cardioversion lead system with internal electrical switching components for unipolar or bipolar sensing of electrograms, pacing at normal pacing voltages and cardioversion or defibrillation. In bipolar embodiments, an indifferent electrode, closely spaced to a sensing and pacing electrode, is coupled in common through the integral switching circuitry to a large surface area cardioversion electrode. In these embodiments, pacing and sensing is accomplished through a pair of conductors extending through the lead system to the closely spaced active and indifferent electrode pair. When cardioversion energy is applied to the indifferent electrode, the cardioversion energy is also directed to the cardioversion electrode through operation of the switching circuitry in response to the magnitude of the applied cardioversion pulse. In unipolar embodiments, a distal sensing and pacing electrode is coupled through integral switching circuitry to a large surface area cardioversion electrode. In these embodiments, only a single conductor extending through the lead to the pacing and sensing electrode is required. When cardioversion energy is applied to the pacing and sensing electrode, the cardioversion energy is also directed to the cardioversion electrode through operation of the switching circuitry in response to the magnitude of the applied cardioversion pulse.

8 Claims, 2 Drawing Sheets

PACING AND CARDIOVERSION LEAD SYSTEMS WITH SHARED LEAD CONDUCTORS

BACKGROUND OF THE INVENTION

This invention relates to electrode leads for use in the detection and control of cardiac bradyarrhythmias and tachyarrhythmias, and particularly to a lead including cardioversion/defibrillation electrodes and pacing/sensing electrodes on a common lead body.

Research to provide an automatic implantable pacemaker/cardioverter/ defibrillator has been in progress for over twenty years and has led to the implantation in recent years of several versions of such systems. Over the same period of time, considerable research and development effort has been expended in the development of cardioversion and defibrillation leads. In this context, both unipolar and bipolar pacing and sensing have been employed. Recently, it has also been disclosed that biphasic cardioversion and defibrillation pulses provide substantial benefits.

The traditional approaches to adding pacing and sensing electrodes to cardioversion/defibrillation leads require a separate conductor for each pacing and sensing electrode and for each independently usable defibrillation electrode. Thus, bipolar sensing typically requires at least three conductors, and in the case of multiple cardioversion/defibrillation electrodes, four or more conductors. In embodiments employing multiple cardioversion/defibrillation electrodes, even unipolar sensing correspondingly typically requires at least three conductors. As the size and complexity of these leads increases with each additional conductor, a reduction of the number of conductors per lead is desirable.

In endocardial leads, a further complication arises. It is believed desirable in many cases to locate a right ventricular cardioversion/defibrillation electrode as close to the apex of the heart as possible. However, placement of one or two sense/pace electrodes at the distal end of the lead (a preferred location) typically results in location of the defibrillation electrode in a less apical location, in order to provide space for the pace/sense electrode or electrodes.

Bipolar sensing has been disclosed to be particularly effective in the detection of "near field" ECGs which are used for arrhythmia detection and or synchronization of delivered cardioversion and defibrillation shocks in some current devices. While workable, it is believed less than optimal to employ a small surface area pace/sense electrode in conjunction with a large surface area cardioversion/defibrillation electrode for sensing the near field ECG. The large surface area cardioversion electrode may extend over or near enough to conduction pathways which reflect both atrial and ventricular originated ECG components. If large enough, the "far field" components can in some cases be detected and confuse the tachyarrhythmia detection circuitry and algorithm of the pulse generator. Consequently, a number of references recommend the use of a separate pair of closely spaced, small surface area pace/sense electrodes for sensing. For example, see U.S. Pat. No. 4,614,192, issued to Imran et al., and U.S. Pat. No. 5,044,375, issued to Bach, et al. It should also be Noted that Implantable pacemaker/cardioverter/defibrillators currently in clinical testing, manufactured by Medtronic, Inc., employ ventricular endocardial leads as generally illustrated in U.S. Pat. No. 5,014,696, issued to Mehra, which include a bipolar electrode pair for sensing, located adjacent the distal end of the lead, and a large surface area coil electrode located proximal to the bipolar pair.

U.S. Pat. No. 4,440,172 describes a number of embodiments of pacing and cardioversion electrodes and leads which provide for unipolar pacing and sensing through the use of endocardial ventricular tip electrodes or an epicardial button electrodes paired with epicardial defibrillation electrodes. In one embodiment, a combined defibrillator-pacer system is depicted where the monophasic defibrillation shocks and pacing pulses are transmitted over the same conductor pair through the lead body but are routed to different electrodes on the basis of their polarity using steering diodes located within the lead. However, this approach would appear to be problematic in the event that biphasic cardioversion/defibrillation pulses were to be employed.

In U.S. Pat. No. 4,499,907, a transvenous, endocardial version lead is described which employs a pair of distal electrodes and a pair of proximal electrodes, which are respectively intended to be lodged in the ventricular apex of the right ventricular chamber of the heart and the superior vena cava. Each pair of electrodes is intended to be electrically connected in common by circuitry within the implantable cardioverter during cardioversion. However during sensing and pacing, the closely spaced distal ventricular electrodes are connected to an ECG sense amplifier and a pacing energy pulse generator. The lead also includes circuitry for limiting the voltage of shocks delivered by the lead. U.S. Pat. No. 4,595,009 discloses switching circuitry which controls the interconnection of the pulse generators, sense amp and electrodes during pacing, sensing and cardioversion in conjunction with a lead generally as illustrated in the '907 patent, but lacking the voltage limiting circuitry.

SUMMARY OF THE INVENTION

For purposes of this application, "cardioversion" is used hereafter in a broad sense, as including the application of relatively high energy and high voltage shocks to the heart to terminate tachyarrhythmias including fibrillation and malignant tachycardias. Similarly, "pacing" is used in a broad sense as including the application of relatively low energy and low voltage pacing impulses to maintain an adequate heart rate or to break a tachycardia by stimulating the patient's heart.

It is an object of the present invention to reduce the total number of lead conductors for connection to a pacing and cardioversion lead which includes an electrode or electrodes for sensing and pacing the heart in addition to one or more large surface area cardioversion electrodes.

In the context of endocardial ventricular leads, it is an object of the present invention to provide an electrode or electrode pair for sensing adjacent the ventricular apex while still providing a cardioversion electrode which also is located as close to the ventricular apex as possible.

These and other objects of the present invention are realized by providing leads having at least one small surface area pacing or sensing electrode closely spaced to a large surface area cardioversion/defibrillation electrode with a conductor extending to said pacing or sensing electrode through the lead body and by incorporating switching circuit means in the lead body which connects the large surface area cardioversion electrode and the smaller surface area pace/sense electrode during delivery of cardiovesion pulses, and otherwise disconnects the large surface electrode from the pacing or sensing electrode. In response to a cardioversion pulse applied to the conductor the switching circuitry automatically electrically connects the cardioversion electrode to the pacing or sensing electrode during delivery of the cardioversion pulse.

In endocardial lead embodiments, a small surface area tip electrode is provided for pacing and sensing. In bipolar embodiments, an indifferent sense electrode is provided which is typically a ring electrode surrounding the lead body a short distance from the tip electrode. In accordance with these endocardial bipolar embodiments of the present invention, a large surface area cardioversion electrode is located on the lead body distal to the indifferent ring electrode. In practice, the tip electrode is located in the right ventricular apex. The inclusion of the indifferent electrode in bipolar embodiments or the tip electrode in unipolar embodiments as part of the effective area of the cardioversion electrode advantageously provides a cardioversion electrode which is effectively located in a more apical position.

The switching circuitry employed in the embodiments of the present invention may include zener diodes singly or in back-to-back configuration, miniaturized transient surge suppression circuits which respond to the applied high voltage cardioversion shock to effectuate such switching for the duration of the shock, or other functionally similar circuitry. In certain embodiments, suppression resistors may also be included as part of the switching circuitry.

BRIEF DESCRIPTION OF THE DRAWINGS

The above and other object and advantages of the present invention will be more clearly understood by reference to the following description, the appended claims and their accompanying drawings, in which like reference numerals designate like parts throughout the figures thereof and wherein:

DETAILED DESCRIPTION OF THE PREFERRED EMBODIMENTS

FIGS. 1-4 and 6 are schematic representations of the electrical interconnection of at least one cardioversion/defibrillation and a pace/sense electrode to a single conductor and connector and employing switching circuitry within the lead which responds to the magnitude of the applied cardioversion shock to direct the shock to the cardioversion/defibrillation electrode commonly with the at least one pace/sense electrode.

Figure 1:
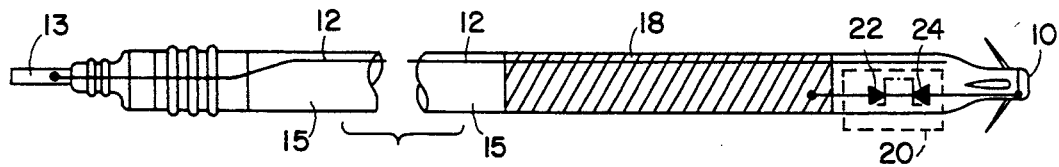
FIG. 1 is a schematic illustration of a first, endocardial, unipolar lead embodiment of the invention.

FIG. 1 illustrates a first, unipolar embodiment of the present invention, schematically illustrating the arrangement of tip electrode 10 and elongated cardioversion electrode 18. In this embodiment, the tip electrode 10 is coupled to the elongated cardioversion electrode 18 through switching circuit 20 which may take the form of back-to-back zener diodes 22, 24.

In the embodiment of FIG. 1, sensing and pacing may take place between the housing of the implantable pacemaker/cardioverter/defibrillator to which the lead is attached and tip electrode 10. Tip electrode 10 is mounted at the distal end of insulative lead body 15 and is coupled to conductor 12, which in turn is coupled to connector 13. Since pacing pulses and ECG signal voltage amplitudes fall far below the breakover voltages of diodes 22, 24, ECG signal contribution from the more proximal end of the elongated cardioversion electrode 18 which may extend 10 or more centimeters along the lead body is not added to the signals picked up by electrode pair 10. When cardioversion shocks are delivered, on the other hand, the terminal 13 is coupled to one of the output terminals of the cardioversion pulse generator, and the tip electrode 10 and the elongated cardioversion electrode 18 are electrically connected together as a single effective electrode by operation of the back-to-back zener diodes 22, 24 which may be selected to break down at 80 to 100 volts on the leading edge of the cardioversion shock.

It will be understood that a second cardioversion electrode or electrode may be also optionally be located on the lead of FIG. 1, for example placed such that it is located in the superior vena cava after implant. However, more typically a second cardioversion electrode and optionally third or fourth cardioversion electrodes will be located on separate leads or on the housing of an associated pacemaker/cardioverter/defibrillator.

Figure 2:
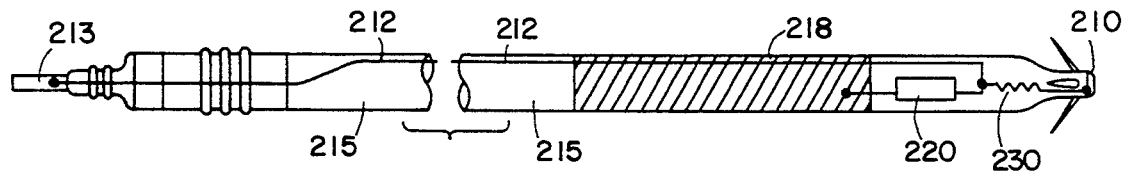
FIG. 2 is a schematic illustration of a second, endocardial, unipolar lead embodiment of the invention.

FIG. 2 illustrates a second embodiment of the present invention, corresponding generally to the embodiment illustrated in FIG. 1, but substituting a transient surge suppressor 220 and an optional resistor 230 for dividing of cardioversion energy between the pace/sense electrode 210 and the cardioversion electrode 218 for the back-to-back zener diodes 22, 24. Such a series resistor 230, having a resistance in the range of 50-100 ohms, would limit current through the electrode 210 during the cardioversion/defibrillation shock and would only attenuate pacing voltage by 5 to 10 percent. Resistor 230 may also optionally be incorporated into the embodiment of FIG. 1, if necessary. Like the embodiment of FIG. 1, only a single conductor 212 is used, connecting electrode 210, which is mounted at the distal end of insulative lead body 215, to connector 213 via resistor 230, with the switching circuitry 220 connecting the cardioversion electrode 218 to the conductor 212.

The transient surge suppressor may advantageously be the model 3B249 TEDD model transient surge suppressor from ABB HAFO or other similar component. This transient surge suppressor is supplied in a miniature three terminal package, is based on thyristor diode structure silicon integrated circuits and is especially well suited as a lightning arrestor for the protection of sensitive SLIC circuitry and telephone line interfaces. The design of this particular component is advantageous in that it provides extremely fast operation in nanoseconds and high current handling capability of more than 150 amps in a small TO 220 package. Customized packages are also available from a manufacturer. Breakover voltage is 60 to 80 volts with a crowbar action and voltage characteristics are asymmetric.

Such a small package transient surge suppressor may be incorporated within the confines of transvenous endocardial pacing and cardioversion lead bodies in a fashion analogous to the mounting of thermistors in temperature sensing leads as in U.S. Pat. No. 4,726,383 issued to Cook et al., incorporated herein by reference in its entirety or may be mounted in a hermetic enclosure similar to those employed to mount pressure transducers, as disclosed in U.S. Pat. No. 4,485,813, issued to Anderson et al. and also incorporated herein by reference in its entirety.

Figure 4:
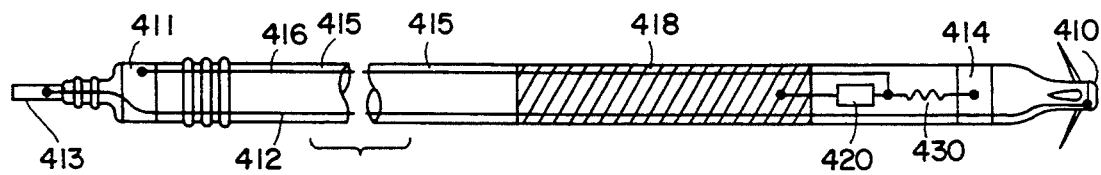
FIG. 4 is a schematic illustration of a fourth, endocardial, bipolar lead embodiment of the invention.
Figure 5:
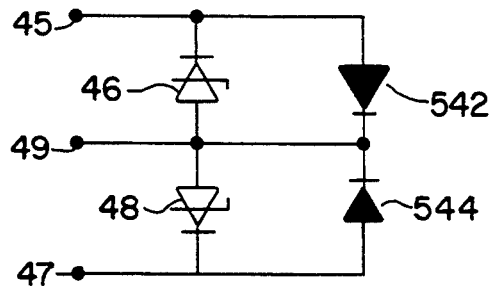
FIG. 5 is a schematic illustration of the surge suppression circuit employed in various embodiments of the present invention.

The transient surge suppressor depicted in more detail in FIG. 5 comprises a pair of back-to-back diodes 542, 544 and back-to-back thyristor elements 546, 548 electrically connected in parallel to one another between terminals 545 and 547. A common terminal pin 549 is provided at the junction of the back-to-back zener diodes and back-to-back thyristor elements which are thus electrically connected together. In the present invention, only the terminals 545 and 547 are employed and connected to points 221, 321 and 225, 325 of the lead embodiments illustrated in FIGS. 2 and 4.

Figure 3:
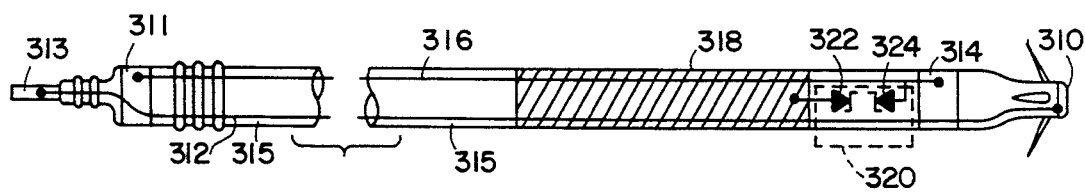
FIG. 3 is a schematic illustration of a third, endocardial, bipolar lead embodiment of the invention.

FIG. 3 illustrates a third embodiment of the present invention, schematically illustrating the arrangement of tip electrode 310, distal ring electrode 314 and elongated cardioversion electrode 318. In this embodiment, the ring electrode 314 is coupled to the elongated cardioversion electrode 318 through switching circuit 320 which may take the form of back-to-back zener diodes 322, 324, in a manner analogous to the interconnection of the tip and cardioversion electrodes as illustrated in FIG. 1. Ring electrode 314 is coupled to connector 311 through conductor 316. Tip electrode 310, which is mounted at the distal end of insulative lead body 315, is coupled to connector 313 through conductor 312.

In the embodiment of FIG. 3, bipolar sensing and pacing may take place between the 0.5 to 3.0 centimeter spaced tip electrode 310 and ring electrode 314 through conductors 312 and 316, respectively. Since pacing pulses and ECG signal voltage amplitudes fall far below the breakover voltages of diodes 322, 324, ECG signal contribution from the more proximal end of the elongated cardioversion electrode 318 which may extend 10 or more centimeters along the lead body is not added to the signals picked up across the bipolar sensing electrode pair 310, 314. When cardioversion shocks are delivered, the terminal 313 is coupled to one of the output terminals of the cardioversion pulse generator, and both the ring electrode 314 and the elongated cardioversion electrode 318 are electrically connected together as a single effective electrode by operation of the back-to-back zener diodes 322, 324.

It will be understood that a second cardioversion electrode or electrode may be also be located on the lead of FIG. 3. However, more typically a second cardioversion electrode and optionally third or fourth cardioversion electrodes will be located on separate leads or on the housing of an associated pacemaker/cardioverter/defibrillator.

The embodiments of FIG. 3, and of FIG. 4 discussed below, are particularly advantageous in eliminating the far-field signal contribution to bipolar sensing which would occur if the cardioversion electrode 318 were paired with tip electrode 310 for sensing, while retaining an apical location for the effective distal end of the cardioversion electrode. In addition, the embodiments of FIGS. 3 and 4 accomplish these desirable results using only two conductors in the lead body.

FIG. 4 illustrates a fourth embodiment of the present invention, corresponding generally to the embodiment illustrated in FIG. 3, but substituting a transient surge suppressor 420 and an optional resistor 430 for dividing of cardioversion energy between the pace/sense electrode 414 and the cardioversion electrode 418 for the back-to-back zener diodes 322, 324, in a manner analogous to the interconnection of the tip and cardioversion electrodes in FIG. 2. As noted above, resistor 430 may be incorporated into the other embodiments depicted as necessary. Ring electrode 414 is coupled to connector 311 through conductor 416. Tip electrode 410, which is mounted at the distal end of insulative lead body 315, is coupled to connector 413 through conductor 412.

Figure 6:
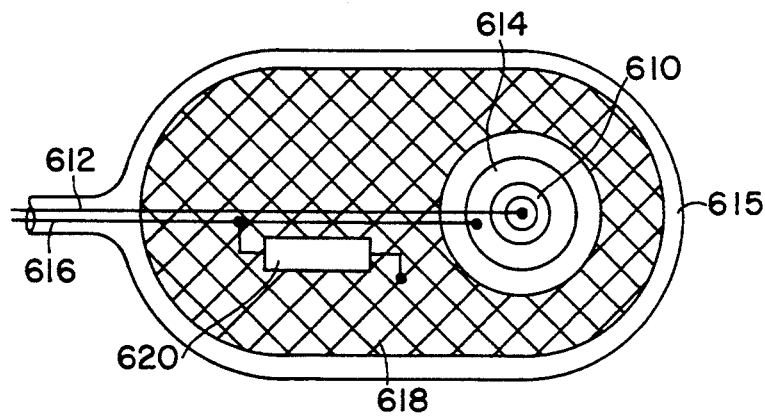
FIG. 6 is a schematic partial illustration of an epicardial bipolar lead embodiment of the invention.

As illustrated in FIG. 6, the concepts of the present invention may also be implemented in epicardial lead embodiments. The lead includes active pacing/sensing electrode 610, indifferent ring electrode 614 and large surface area cardioversion electrode 618, all of which are mounted to insulative base pad 615. The switching circuit 620 is connected between cardioversion electrode 618 and ring electrode 614. The switching circuit 620 may comprise the surge suppressor circuit of FIG. 5. Ring electrode 614 is centrally located, and current densities are expected to be lower in this are of the electrode, so no limiting resistor is included. The surge suppressor 620 is connected between the conductor 616 and the epicardial patch cardioversion electrode 618 which is mounted on a pad or support 640. The pace/sense electrodes 610 and 614 are connected to the conductors 612 and 616 within lead body.

Figure 7:
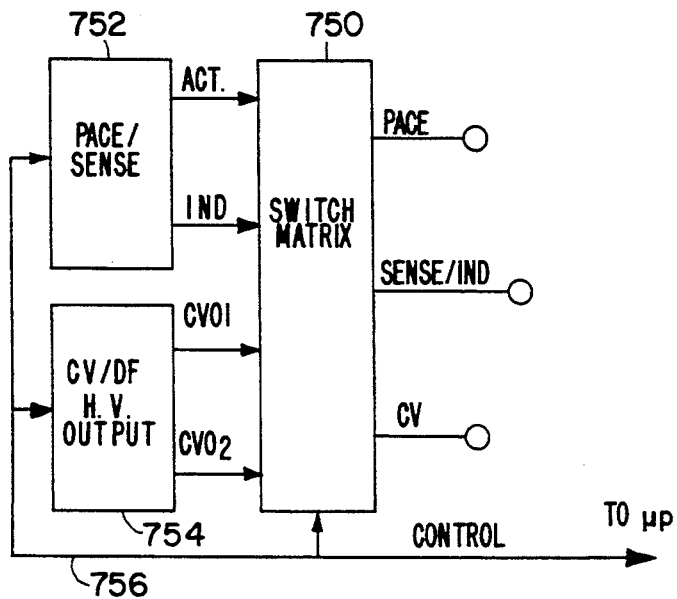
FIG. 7 is a simplified input/output circuit for a combined pacemaker-cardioverter-defibrillator usable with the leads of FIGS. 1-4 and 6.

FIG. 7 illustrates a simplified input/output switching circuit for a combined function pacemaker-cardioverter-defibrillator using any one of the above described shared conductor pace/sense and cardioversion leads is depicted. The switching circuit 750 is adapted to selectively couple the active (ACT) and indifferent (IND) output/input terminals of the pace/sense circuit 752 and the high voltage cardioversion/defibrillation output terminals CV01, CV02 of the high voltage output circuit 754 to the terminals of the leads illustrated in FIGS. 1-4 and 6 and to a further cardioversion electrode. Control signals applied via control bus 756 to blocks 750, 752, 754 from a microprocessor based control system of the type presently employed in current implantable pacemaker/cardioverter/defibrillators to control operating modes and parameters and control the selection of the lead terminals for each of the pace, sense and cardioversion functions. For example, a system as disclosed in U.S. patent application Ser. No. 07/750,679, filed Aug. 21, 1991 by Bardy et al., incorporated herein by reference in its entirety.

In the embodiments illustrated in FIGS. 1 and 2, during pacing and sensing, the Pace/sense circuitry 752 is connected to the lead connector and to a remote indifferent electrode, typically the housing of the pacemaker/cardioverter/defibrillator or one of the cardioversion electrodes not located on the lead body. During cardioversion, the pace/sense circuitry 752 is disconnected from the lead and the cardioversion outputs CV01 and CV02 are connected to the lead connector and to a second cardioversion electrode.

In the embodiments illustrated in FIGS. 3,4 and 6, during pacing and sensing, the Pace sense circuitry 752 is connected to the lead connector coupled to the ring electrode and to the lead connector coupled to the tip electrode. During cardioversion, the pace/sense circuitry 752 is disconnected from the lead and the cardioversion outputs CV01 and CV02 are connected to the lead connector coupled to the indifferent ring electrode and to a second cardioversion electrode.

Other modifications of the embodiments of the pacing and cardioversion electrode systems of the present invention will become readily apparent to those skilled in the argument in light of the foregoing disclosure, which should be considered exemplary, rather than limiting with regard to the scope of the claims that follow.

What is claimed is:

1. A cardioversion and pacing lead for implantation in or on a human heart, comprising:

an elongated insulated lead body;

a first conductor, having a proximal end and a distal end, mounted in said lead body;

a second conductor, having a proximal end and a distal end, mounted within said lead body, insulated from said first conductor;

a first connector, coupled to the proximal end of said first conductor;

a second connector, coupled to the proximal end of said second conductor;

a first electrode, exposed to the exterior of said lead body and coupled to the distal end of said first conductor for applying electrical energy to and sensing heart signals from heart tissue;

a second electrode exposed to the exterior of said lead body and coupled to the distal end of said second conductor for applying electrical energy to and sensing heart signals from heart tissue;

a third electrode exposed to the exterior of said lead body for applying electrical energy to heart tissue; and switching means within said lead body coupled between said second conductor and said third electrode for directing the electrical energy of a cardioversion pulse applied to said second connector in common to said second and third electrodes and to said heart tissue, while preventing the electrical energy of a pacing pulse applied to said first and second connectors from being directed to the third electrode.

2. A cardioversion and pacing lead according to claim 1 further comprising energy-limiting means coupled to said second electrode and conductor for preventing the electrical energy of a said cardioversion pulse from exceeding a maximum energy level at said second electrode.

3. A cardioversion and pacing lead according to claim 1 wherein said switching means further comprises a pair of series connected, back-to-back zener diodes having breakover conduction voltages selected to switch said diodes into conduction only when a cardioversion voltage and current is applied to said second connector.

4. A cardioversion and pacing lead according to claim 3 wherein said switching means further comprises a thyristor and zener diode surge suppression circuit.

5. A cardioversion and pacing lead for implantation in or on a human heart, comprising:

an elongated insulated lead body;

a conductor, having a proximal end and a distal end, mounted in said lead body;

a connector, coupled to the proximal end of said conductor;

a first electrode, exposed to the exterior of said lead body and coupled to the distal end of said conductor for applying electrical energy to and sensing heart signals from heart tissue;

a second electrode exposed to the exterior of said lead body for applying electrical energy to heart tissue; and switching means within said lead body, responsive to the delivery of a cardioversion pulse to said first electrode, coupled between said first and second electrodes for applying electrical energy of a cardioversion pulse applied to said first electrode to said second electrode and to said heart tissue, while preventing application of electrical energy of a pacing pulse applied to said first electrode to said second electrode.

6. A cardioversion and pacing lead according to claim 5 further comprising energy-limiting means coupled between said first and second electrodes for preventing electrical energy of a said cardioversion pulse from exceeding a maximum energy level at said first electrode.

7. A cardioversion and pacing lead according to claim 5 wherein said switching means further comprises a pair of series connected, back-to-back zener diodes having breakover conduction voltages selected to switch said diodes into conduction only when a cardioversion voltage and current is applied to said first electrode.

8. A cardioversion and pacing lead according to claim 7 wherein said switching means further comprises a thyristor and zener diode surge suppression circuit.

* * * * *